United States Patent
Kimura et al.

(10) Patent No.: US 9,289,271 B2
(45) Date of Patent: Mar. 22, 2016

(54) DENTAL HANDPIECE

(75) Inventors: Takao Kimura, Kanuma (JP); Masanori Mizunuma, Kanuma (JP); Keita Yokochi, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 13/469,313

(22) Filed: May 11, 2012

(65) Prior Publication Data

US 2012/0288823 A1 Nov. 15, 2012

(30) Foreign Application Priority Data

May 13, 2011 (JP) .................. 2011-108545

(51) Int. Cl.
*A61C 1/12* (2006.01)
*A61C 1/08* (2006.01)
*A61C 1/10* (2006.01)

(52) U.S. Cl.
CPC ... *A61C 1/12* (2013.01); *A61C 1/08* (2013.01); *A61C 1/10* (2013.01)

(58) Field of Classification Search
USPC .......... 433/103–135, 146–147; 403/348–349, 403/325–326; 606/79–80, 84; 175/327–435; 408/199–233
See application file for complete search history.

(56) References Cited

U.S. PATENT DOCUMENTS

| | | | | | |
|---|---|---|---|---|---|
| 1,534,817 | A | * | 4/1925 | Thiedemann et al. | 433/116 |
| 2,527,256 | A | * | 10/1950 | Jackson | 403/319 |
| 3,909,946 | A | * | 10/1975 | Watanabe | 433/126 |
| 5,741,084 | A | * | 4/1998 | Del Rio et al. | 403/349 |
| 6,161,244 | A | * | 12/2000 | Jeannet et al. | 15/167.1 |
| 2009/0317758 | A1 | | 12/2009 | Duineveld et al. | |

FOREIGN PATENT DOCUMENTS

| | | |
|---|---|---|
| EP | 0 525 649 A1 | 2/1993 |
| JP | 5-23352 | 2/1993 |

* cited by examiner

*Primary Examiner* — Edward Moran
(74) *Attorney, Agent, or Firm* — Jason D. Voight

(57) ABSTRACT

A dental handpiece has a head section, a neck section, a grip section connected to the grip section, and a drive unit connected to the grip section. The handpiece also has a detent unit for preventing relative rotation between the neck and grip sections. The detent unit includes a detent pin arranged axially slidably in the grip section, a spring for biasing the pin proximally so that the distal end of the pin is arranged inside the grip section in a rest position, and a catch formed at the proximal end of the neck section for receiving the pin for engagement. When the drive unit is brought into connection to the grip section, the pin is pressed distally to project out of the grip section into engagement in the catch, to thereby prevent relative rotation between the neck section and the grip section.

7 Claims, 8 Drawing Sheets

DENTAL HANDPIECE

This application claims priority to Japanese application 2011-108545, filed May 13, 2011.

FIELD OF ART

The present invention relates to a dental handpiece, in particular a dental handpiece in which a grip section is detachably connected to a neck section, and a drive unit is detachably connectable to the grip section.

BACKGROUND ART

A dental handpiece generally has a head section having a rotary shaft to which a dental tool is attached, a neck section of a generally cylindrical shape extending proximally from the head section and having a drive transmission shaft extending therein, and a grip section of a generally cylindrical shape detachably connected to the proximal end of the neck section and having a rotary shaft extending therein. A drive unit having a motor is detachably connectable to the proximal end of the grip section to operatively link the motor to the rotary shaft. The motor drives the rotary shaft in the grip section, and via the drive transmission shaft in the neck section, rotates the rotary shaft in the head section at a high speed. Some types of such dental handpieces are configured such that the neck section and the grip section are detachably connected via a various kinds of connecting means, and the neck section, the drive transmission shaft, and the grip section may be disassembled for maintenance, such as cleaning.

FIG. 10 shows an example of such a conventional handpiece. In this handpiece 7, the neck section 72 and the grip section 73 are detachably connected via a cylindrical coupling member 74. The coupling member 74, for example as shown in JP-5-23352-A, has on the inner surface in its distal portion a notch engageable to a projection provided in the proximal end portion of the neck section, and on the inner surface in its proximal portion an internal thread to be meshed with an external thread provided on the circumferential surface of the distal portion of the grip section. The neck section 72 and the grip section 73 are assembled by inserting the proximal end of the neck section 72 into the distal end of the grip section 73, and rotating the coupling member 74 clockwise (as seen proximally from the neck section 72) to tighten the threads. In reverse, the neck section 72 and the grip section 73 are disassembled by rotating the coupling member 74 counterclockwise (as seen proximally from the neck section 72) to sufficiently loosen the threads as shown in FIG. 10(A), and pulling apart the neck section 72 and the grip section 73 in the axial direction as shown in FIG. 10(B). Such a coupling member 74 can securely fix the neck section 72 and the grip section 73.

However, with such a connecting mechanism between the neck section and the grip section of the conventional handpiece, the assembly/disassembly of the neck section and the grip section requires repeated screwing up/down of the threaded coupling member, which is laborious and inconvenient. In addition, users have different powers to tighten the coupling member, and in some cases the coupling member may not be tightened sufficiently and may be accidentally rotated and loosened due to the vibration occurring during use of the handpiece.

SUMMARY OF THE INVENTION

The present invention aims to solve such problems of the conventional handpiece.

It is an object of the present invention to provide a detent mechanism for a dental handpiece capable of easily and securely preventing/allowing relative rotation between the neck section and the grip section in a single action, while allowing use of various connecting means including conventional ones for securely connecting/disconnecting the neck section and the grip section.

It is another object of the present invention to provide connecting means for a dental handpiece suitable for connecting/disconnecting the neck section and the grip section in a single action and usable in combination with the detent mechanism.

According to the present invention, there is provided a dental handpiece having a head section to which a dental treatment tool is to be attached, a neck section of a generally cylindrical shape extending proximally from the head section, and a grip section of a generally cylindrical shape detachably connected at its distal end to a proximal end of the neck section via connecting means, wherein a drive unit is detachably connectable to a proximal end of the grip section, said handpiece comprising detent means for preventing relative rotation between the neck section and the grip section, said detent means comprising:

a detent pin arranged in the grip section slidably in the axial direction of the grip section, spring means for biasing the detent pin proximally so that a distal end of the detent pin is arranged inside the grip section in a rest position, and catch means formed at a proximal end of the neck means for receiving a distal end of the detent pin for engagement, wherein said detent means is arranged such that, when the drive unit is brought into connection to the proximal end of the grip section, the detent pin is pressed distally to project at its distal end out of a distal end face of the grip section into a position to engage the catch means, to thereby prevent relative rotation between the neck section and the grip section.

The detent pin may preferably be arranged in the grip section such that the proximal end of the detent pin in the rest position is projected from a proximal end face of the grip section. In this case, when the drive unit is brought into connection to the proximal end of the grip section, the detent pin is pressed distally by a distal end face of the drive unit to project at its distal end out of the distal end face of the grip section.

Alternatively, the detent pin may be arranged in the grip section such that the proximal end of the detent pin in the rest position is located inside the grip section. In this case, the drive unit may have a pressing member extending from its distal end face and insertable into the grip section for pressing the detent pin. When the drive unit is brought into connection to the proximal end of the grip section, the detent pin is pressed distally by the pressing member of the drive unit to project at its distal end out of the distal end face of the grip section.

Further, the neck section may have an opening at its proximal end, and the grip section may have at its distal end a generally cylindrical projection fittable in the neck section through the opening. The connecting means may include a pair of engaging pins projecting symmetrically on a circumferential surface of the projection of the grip section, and a pair of engagement grooves provided symmetrically on the inner surface of the cylindrical neck section near the opening for receiving the engaging pins. Each engagement groove may have an engaging portion, an entry portion, and a guide portion, the engaging portion being capable of receiving and engaging one of the engagement pins in a lock position, the entry portion being opened to the opening of the neck section and extending in the axial direction of the neck section, said guide portion extending from the end of the entry portion opposite to the opening in a circumferential direction of the neck portion for guiding the engaging pin from the entry portion to the engaging portion. In this case, the neck section and the grip section may be connected by inserting the projection of the grip section into the neck section through the opening, with each engaging pin aligned with the entry portion of each engagement groove, and relatively rotating the neck section and the grip section with the guide of the engaging pin engaged in the guide portion, until the engaging pin fits in the engaging portion in the lock position.

The entry portion of at least one of the engagement grooves may be used as the catch means for receiving the distal end of the detent pin. In this case, the detent pin engages the entry portion, with the neck section and the grip section connected by means of engagement of the engaging pins in the engaging portions.

With the dental handpiece according to the present invention having such a structure, the neck section and the grip section connected with each other with connecting means may securely be prevented from relative rotation, by a single action of bringing the drive unit into connection to the proximal end of the grip section. Further, by associating the detent means with the release of connecting means, the connection between the neck section and the grip section via the connecting means may securely be fixed.

In reverse, the neck section and the grip section prevented from relative rotation by means of the detent means may securely be released for relative rotation by a single action of detaching the drive unit from the grip section. By the release of the detent means, the connecting means may be released to allow disassembly of the neck section and the grip section.

BRIEF DESCRIPTION OF THE DRAWINGS

FIG. 9 illustrates how to prevent the neck section and the grip section from relative rotation, by connecting the drive unit to the grip section, wherein FIG. 9(A) shows the grip section and the drive unit being connected to the grip section, FIG. 9(B) shows the grip section and the drive unit connected with each other, and FIG. 9(C) is an enlarged view of the main part of the connection between the neck section and the grip section circled in FIG. 9(B) after the drive unit is connected to the grip section.

PREFERRED EMBODIMENTS OF THE INVENTION

The present invention will now be explained in detail.

Figure 1:
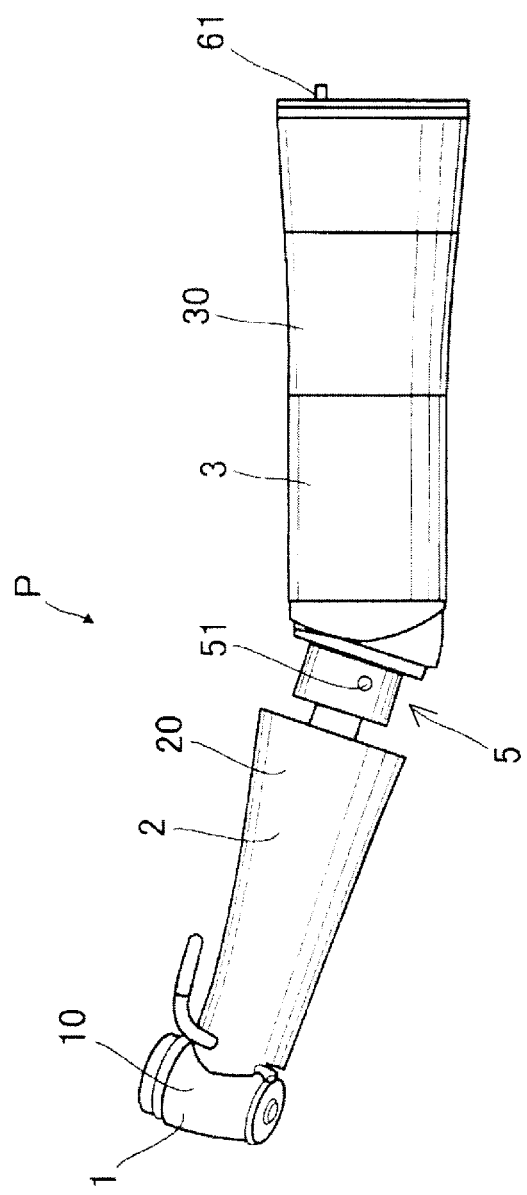
FIG. 1 is a side view, showing the overall appearance, of the dental handpiece according to one embodiment of the present invention.
Figure 9:
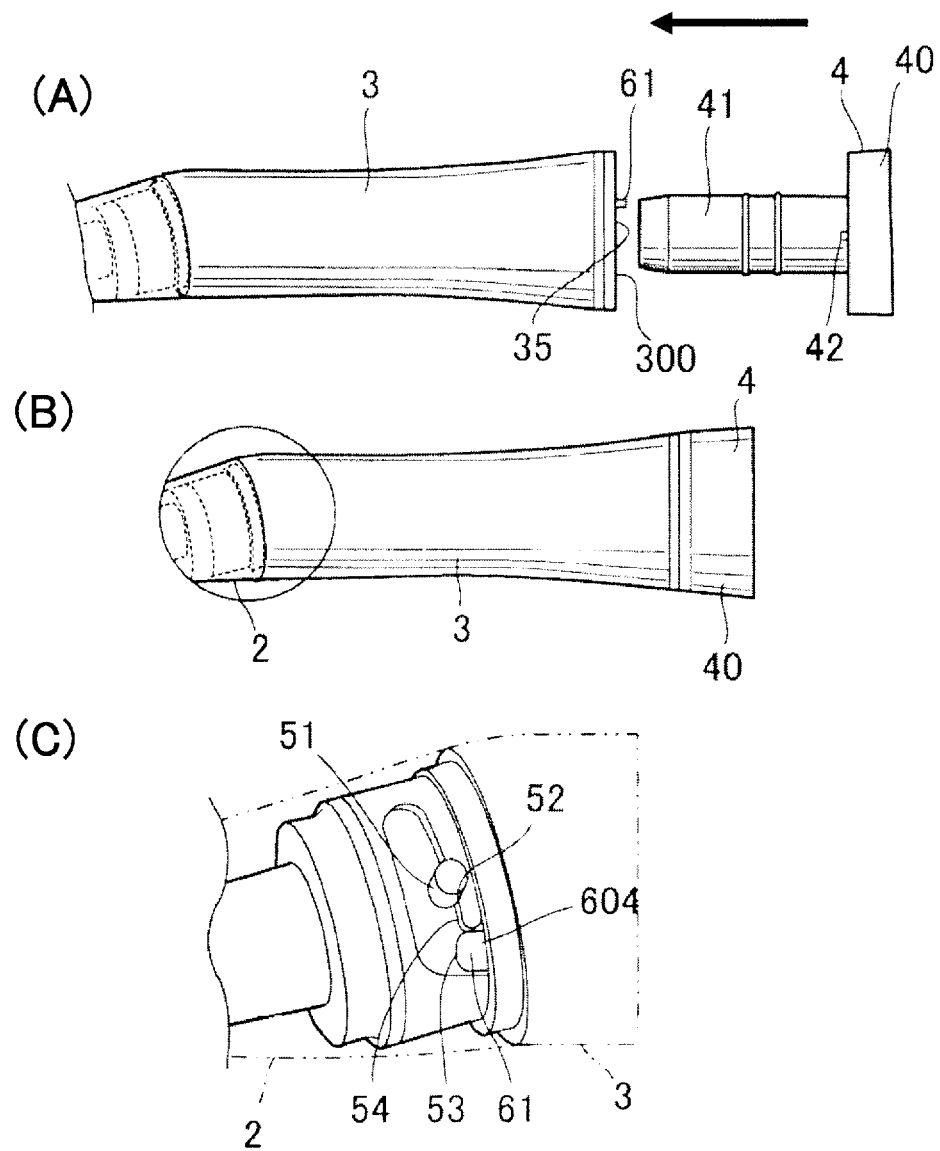
Figure 10:
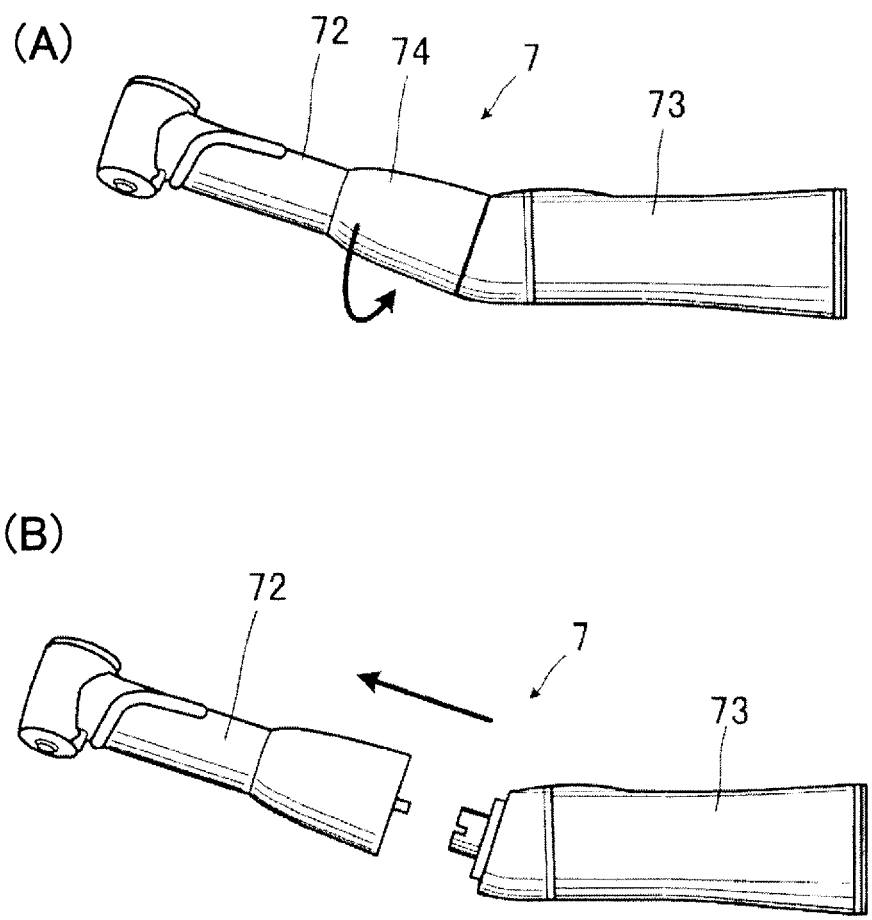
FIG. 10 illustrates how to disconnect the neck section from the grip section of a conventional dental handpiece.

Referring to FIG. 1, which shows the overall appearance of a dental handpiece P of the present invention, and FIGS. 2 to 7, which show the structures of various parts of the dental handpiece P, the dental handpiece P has a head section 1 to which a dental tool is to be attached, a neck section 2 of a generally cylindrical shape extending proximally from the head section 1, and a grip section 3 of a generally cylindrical shape detachably connected to the proximal end of the neck section 2 via connecting means 5. A drive unit 4 (FIG. 9) is detachably connectable to the proximal end of the grip section 3.

The head section 1 has a generally cylindrical head housing 10 and a rotary shaft (not shown) accommodated in the head housing 10.

The neck section 2 extends proximally from the head section 1 and has a generally cylindrical neck housing 20 and a drive transmission shaft (not shown) extending inside the neck housing 20 and operatively linked to the rotary shaft in the head section 1. The neck section 2 has an opening 200 at the proximal end of the neck housing 20, to which the grip section 3 is to be connected.

Figure 2:
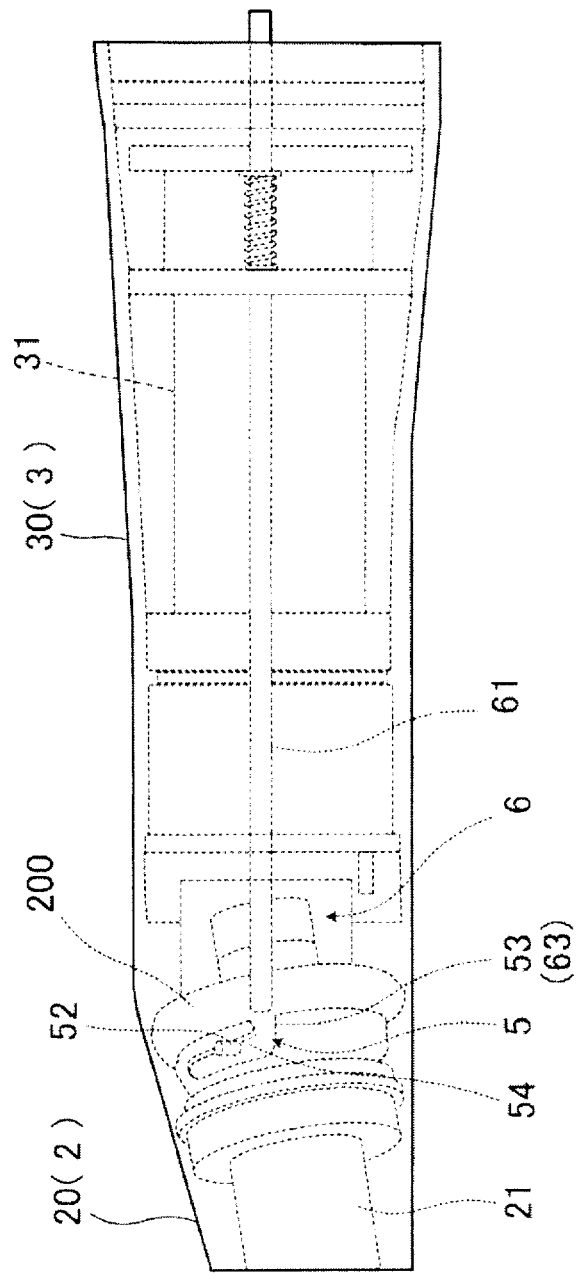
FIG. 2 is an enlarged side view, partially transparent, of the main part of the neck and grip sections of the handpiece of FIG. 1.
Figure 3:
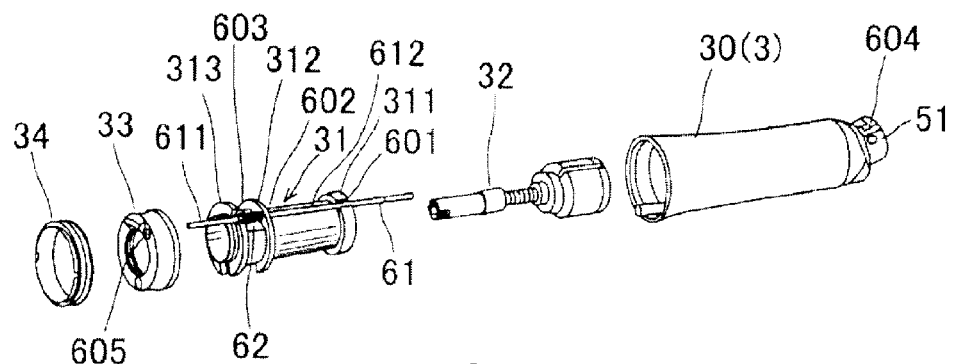
FIG. 3 is an exploded perspective view, showing the internal structure, of the grip section of the handpiece of FIG. 1.

The grip section 3 has a generally cylindrical grip housing 30 and a rotary shaft 32 extending inside the grip housing 30. As shown in FIGS. 2 and 3, a rear joint 31 is accommodated in the grip housing 30, and the rotary shaft 32 extends through the rear joint 31 and operatively linked to a drive source.

The rear joint 31 has on its outer surface a plurality of ring parts which abut the inner surface of the grip housing 30, i.e., a front ring 311 located at the distal end of the rear joint 31, a middle ring 312 located in the middle of the rear joint closer to its proximal end, and a rear ring 313 located at the proximal end of the rear joint 31. The rings 311, 312, 313 assist the rear joint 31 to be positioned in the grip housing 30 coaxially with the longitudinal axis of the grip section 3. The rear joint 31 fits in the proximal end portion of the grip housing 30, and fixedly held therein via a fixing ring 33, which is fixed in the grip housing 30 with an annular fastening screw 34 fastened to the threads provided on the inner surface of the grip housing 30 in the proximal end portion.

Figure 4:
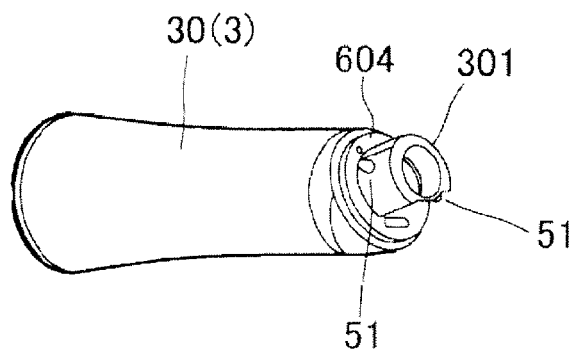
FIG. 4 is a perspective view of the grip section of the handpiece of FIG. 1, showing its external structure from the distal side.
Figure 5:
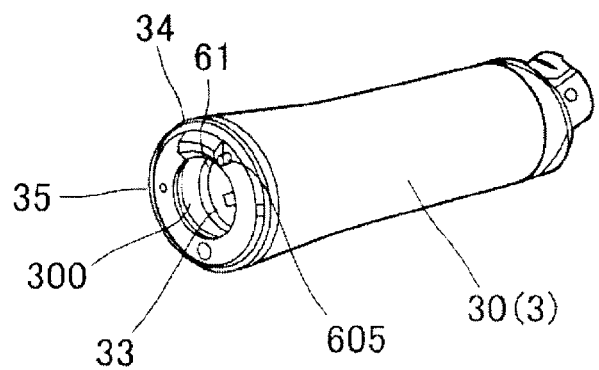
FIG. 5 is a perspective view of the grip section of the handpiece of FIG. 1, showing its external structure from the proximal side.

The distal end of the grip housing 30 is to be connected to the neck section, and, as shown in FIG. 4, is provided with a generally cylindrical projection 301, which is fittable in the neck housing 20 through the opening 200 in the proximal end of the neck section 2. The proximal end of the grip housing 30 is to be connected to the drive unit 4, and, as shown in FIG. 5, has an opening 300 formed with the fixing ring 33 and the fastening screw 34 and communicating into the rear joint 31. In the proximal end face of the fixing ring 33 defining the opening 300 at the proximal end of the grip housing 30, a positioning hole 35 is provided for assisting positioning of the drive unit 4 at a predetermined circumferential angle when assembled with the grip section 3.

The drive unit 4 (FIG. 9) has a generally cylindrical motor housing 40 and a motor unit (not shown) accommodated inside the motor housing 40. The motor unit has an insert 41, which projects out of the distal end face of the motor housing 40 in its center. On the distal end face of the motor housing 40 beside the insert 41, a positioning pin 42 projects for assisting positioning of the grip section 3 at a predetermined circumferential angle when assembled with the drive unit 4.

The insert 41 on the distal end face of the drive unit 4 is insertable into the opening 300 in the proximal end face of the grip section 3, with the positioning pin 42 engaging in the positioning hole 35 to guide the distal end face of the drive unit 4 to surface-contact with the proximal end face of the grip section 3 at a predetermined circumferential angle relative to each other. In this way, the drive unit 4 is connectable to the proximal end of the grip section 3 while the insert 41 of the drive unit 4 is operatively linked to the rotary shaft in the grip section 3.

The neck section 2 and the grip section 3 are connected via connecting means 5. Any type of suitable connecting means, including conventional types, may be used as the connecting means 5. In this embodiment, the connecting means 5 includes, on one hand, a pair of engaging pins 51 projecting symmetrically on the circumferential surface of the projection 301 of the grip section 3, as shown in FIG. 4. The connecting means 5 further includes, on the other hand, a pair of engagement grooves provided symmetrically on the inner surface of the neck housing 20 near the opening 200, as shown in FIGS. 2 and 9(C).

Each engagement groove has an engaging portion 52, an entry portion 53, and a guide portion 54. The engaging portion 52 is capable of receiving and engaging the engaging pin 51 on the projection 301 of the grip section 30 in a lock position, and may be, for example, in the form of a semicircular cut. The entry portion 53 opens to the opening 200 and distally extends therefrom in the axial direction of the neck section 2. The guide portion 54 extends from the end of the entry portion 53 opposite to the opening 200, in the circumferential direction of the neck section 2 for guiding the engaging pin 51 from the entry portion 53 to the engaging portion 52. The two guide portions 54 of the pair of engagement grooves extend in the same circumferential direction of the neck portion 2. The guide portion 54 has a slanted cross-sectional shape of a particular angle in order to guide the engaging pin 51 to draw up the distal end face of the grip housing 30 and the proximal end face of the neck housing 20 together into contact with each other.

With the connecting means 5 of such a structure, the neck section 2 and the grip section 3 may be connected by inserting the projection 301 of the grip section 3 into the neck housing 20 through the opening 200, with each engaging pin 51 on the projection 301 aligned with the entry portion 53 of the engagement groove, and relatively rotating the neck section 2 and the grip section 3 with the guide of the engaging pin 51 engaged in the guide portion 54 of the engaging groove until the engaging pin 51 fits in the engaging portion 52, which is the lock position.

Figure 6:
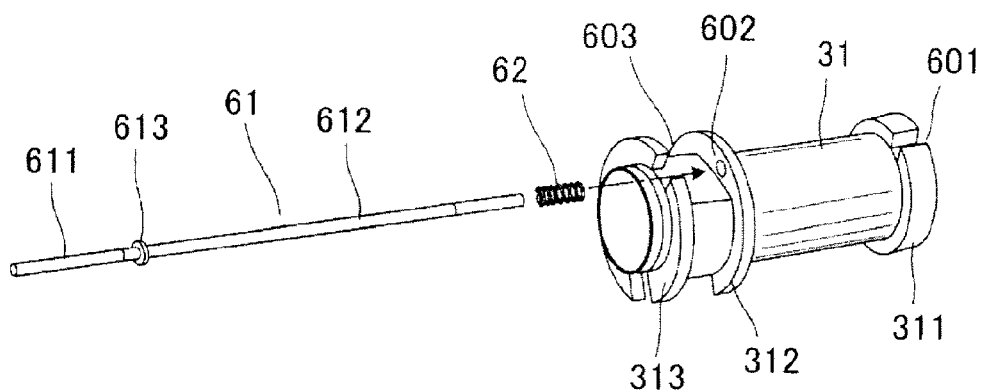
FIG. 6 is a perspective view, partially exploded, of the detent pin and the rear joint to which the detent pin is attached, of the handpiece of FIG. 1.
Figure 7:
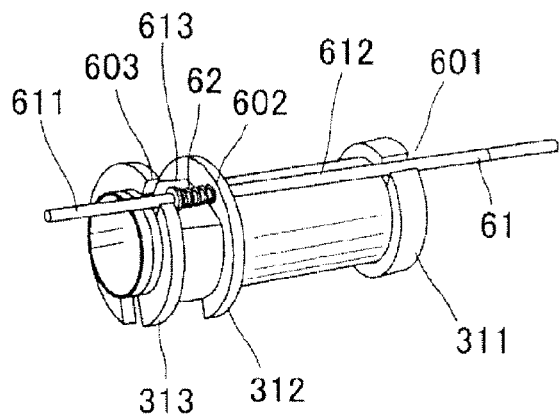
FIG. 7 is a perspective view of the detent pin and the rear joint of FIG. 6 in the assembled state.

The handpiece P of the present invention has a detent means 6 for preventing relative rotation of the neck section 2 and the grip section 3. This detent means 6 may be associated with the connecting means 5. The detent means 6 includes, as shown in FIGS. 3, 6, and 7, a detent pin 61 slidably disposed in the axial direction of the grip section 3 between the inner surface of the grip housing 30 and the pin guides 601, 602, 603 on the rear joint 31, and a spring 62 biasing the detent pin 61 toward the proximal end of the grip section 3. The detent means 6 further includes, as shown in FIG. 2, catch means 63 in the form of a slit provided at the proximal end of the neck section 2 facing to the grip section 3, for receiving the distal end of the detent pin 61 therein for engagement.

As shown in FIG. 6, the detent pin 61 has a larger diameter portion 611 in its proximal portion, a smaller diameter portion in the rest of the detent pin 61, and a flange 613 disposed between the larger diameter portion 611 and the smaller diameter portion 612. In the alternative, the detent pin 61 may have an even diameter throughout its length, and do not have to have larger and smaller diameter portions.

The spring 62 is a coil spring in this embodiment, and is disposed around the smaller diameter portion of the detent pin 61 distal to the flange 613.

As shown in FIG. 6, coaxial pin guides 601, 602, 603 are provided in the rings 311, 312, 313, respectively, of the rear joint 31 to be arranged in the grip housing 30. That is, the pin guide 601 is formed as a channel in the front ring 311 for allowing passage of the smaller diameter portion 612 of the detent pin 61, the pin guide 602 is formed as a hole 602 in the middle ring 312 for allowing passage of the smaller diameter portion 612, and the pin guide 603 is formed as a channel in the rear ring 313 for allowing passage of the larger diameter portion 611 of the detent pin 61.

As shown in FIG. 4, a pin hole 604 is provided through the distal end face of the grip section 3 at a position close to the projection 301 for allowing projection of the detent pin 61 therethrough. As shown in FIG. 5, a pin hole 605 is provided facing to the pin hole 604 through the fixing ring 33 fastened in the proximal end of the grip section 3 at a position close to the opening 300 for allowing projection of the detent pin 61 therethrough.

As shown in FIG. 7, the detent pin 61, having a coil spring 62 arranged around the smaller diameter portion 612 distal to the flange 613, is disposed extending through the rings 311, 312, 313 of the rear joint 31 such that the smaller diameter portion 612 extends through the pin guide 601 in the front ring 311 and the pin guide 602 in the middle ring 312, and the larger diameter portion 611 extends through the pin guide 603 in the rear ring 313. In this assembly, the coil spring 62 is compressed between the flange 613 and the middle ring 312 to normally bias the detent pin 61 toward the proximal end of the rear joint 31, so that the flange 613 is pressed against the rear ring 313 around the channel 603 and a predetermined length of the larger diameter portion 611 extends proximally out of the proximal end of the rear joint 31 in the rest position.

The rear joint 31 with the detent pin 61 attached thereto in this way is fixed in the grip housing 30 by inserting the rear joint 31 into the grip housing 30, with the pin guides 601, 602, 603 axially aligned with the pin holes 604, 605 of the grip section 3, fitting the fixing ring 33 in the proximal end of the grip housing 30 with the larger diameter portion 611 of the detent pin 61 extends through the pin hole 605, and fastening the annular fastening screw 34 into the proximal end of the grip housing 30.

In this way, the detent pin 61 is arranged axially slidably in the grip housing 30. The arrangement of the detent pin 61 is such that, when the detent pin 61 is pressed in the distal direction of the grip section 3, a predetermined length of the smaller diameter portion 612 extends out of the pin hole 604 in the distal end face of the grip section 3.

More specifically, in this embodiment, the detent pin 61 has such a length that at least one end of the detent pin 61 extends out of either end of the grip housing 30, and the larger diameter portion 611 normally (in the rest position) extends out of the pin hole 605 in the proximal end face of the grip section 3 under the biasing force of the coil spring 62 as shown in FIG. 5. When the projected proximal end of the detent pin 61 is pressed in the distal direction of the grip section 3, the proximal end of the detent pin 61 is embedded in the pin hole 605 in the proximal end face of the grip section 3, while the distal end of the detent pin 61 projects out of the pin hole 604 in the distal end face of the grip section 3.

On the other hand, on the end face of the neck section 2 to be connected to the grip section 3, the catch means 63 is provided for receiving the distal end of the detent pin 61 therein for engagement. In this embodiment as shown in FIG. 2, the detent means 6 is associated with the connecting means 5, and the entry portion 53 of one of the pair of engagement grooves, which is cut out from the opening 200 of the neck section 2, is used as the catch means 63 for receiving the detent pin 61. With the neck section 2 and the grip section 3 connected in a locked position by means of the engagement of the engaging pins 51 in the engaging portions 52, the detent pin 61 faces to and aligned with the entry portion 53 of the engagement groove.

With this structure, the neck section 2 and the grip section 3 are prevented from relative rotation when the drive unit 4 is connected to the proximal end of the grip section 3. In this embodiment, by bringing the drive unit 4 into connection to the proximal end of the grip section 3, the distal end face of the motor housing 40 distally presses the proximal end of the detent pin 61, which has extended out of the proximal end face of the grip section 3. This causes the distal end face of the detent pin 61 to project from the distal end face of the grip section 3 through the pin hole 604 and to enter the catch means 63 of the neck section 2, which is also the entry portion 53 of one of the engagement grooves in this embodiment.

Before assembly of the neck section 2, the grip section 3, and the drive unit 4, the proximal end of the detent pin 61 is projected out of the pin hole 605 in the proximal end face of the grip section 3, whereas the distal end of the detent pin 61 is retracted into and embedded in the pin hole 604 in the distal end face of the grip section 3 in this embodiment. For connecting the grip section 3 to the neck section 2, the projection 301 of the grip section 3 is inserted into the neck housing 20 through the opening 200, while a pair of engaging pins 51 are aligned with and inserted into the entry portions 53 of a pair of engagement grooves. Then the neck section 2 is rotated clockwise (as seen proximally from the neck section 2) relative to the grip section 3, with the guide of each engaging pin 51 travelling from the entry portion 53 through the guide portion 54, until the engaging pin 51 fits in the engaging portion 52. These series of steps are completed in a single action.

In this way, the grip section 3 is properly positioned relative to the neck section 2 by means of the engagement of the engaging pins 51 in the engaging portions 52, and is fixedly connected to the neck section 2 in the locked position. In this state, the neck section 2 and the grip section 3 cannot be pulled apart from each other in the axial direction.

After the grip section 3 is thus connected to the neck section 2, a drive unit 4 is connected to the grip section 3. As shown with the arrow in FIG. 9(A), the insert 41 of the drive unit 4 is inserted into the opening 300 of the grip section 3 until the distal end face of the drive unit 4 surface-contacts with the proximal end face of the grip section 3, with the guide of the positioning pin 42 being inserted into the positioning hole 35. Here, the distal end face of the drive unit 4 contacts and distally presses the proximal end of the detent pin 61, which has been projected from the proximal end face of the grip section 3. The detent pin 61 is slid distally in the grip section 3 to project out of the pin hole 604 in the distal end face. With the distal end face of the drive section 4 surface-contacting the proximal end face of the grip section 3 as shown in FIG. 9(B), the insert 41 is operatively linked to the rotary shaft inside the grip section 3, while the distal end of detent pin 61 projects out of the pin hole 604 and enters the entry portion 53 of one of the engagement grooves in the neck section 2. These series of steps are completed in a single action.

In this way, the neck section 2 and the grip section 3 are prevented from relative rotation by means of the engagement between the detent pin 61 and the entry portion 53. In this state, the engagement of each engaging pin 51 in the corresponding engaging portion 52 of the engagement grooves is fixed to secure the connection between the neck section 2 and the grip section 3. This firm fixture between the neck section 2, the grip section 3, and the drive unit 4 prevents the handpiece P from being disassembled in use.

When the neck section 2, the grip section 3, and the drive unit 4 are to be disassembled for maintenance, such as cleaning after use of the handpiece P, the above procedures may be followed in reverse. Such a series of reverse steps are also completed in a single action.

That is, when the drive unit 4 is drawn out of the grip section 3, the pressure imposed by the distal end face of the drive unit 4 on the proximal end of the detent pin 61 is released. The detent pin 61 is thus slid proximally under the force of the coil spring 62, and the distal end of the detent pin 61 is retracted through the pin hole 604 into the interior of the grip section 3, while the proximal end of the detent pin 61 projects out of the pin hole 605 in the proximal end face of the grip section 3. In this way, the engagement of the detent pin 61 in the entry portion 53 of the engagement groove of the neck section 2 is released, and consequently the neck section 2 and the grip section 3 are released for relative rotation.

Figure 8:
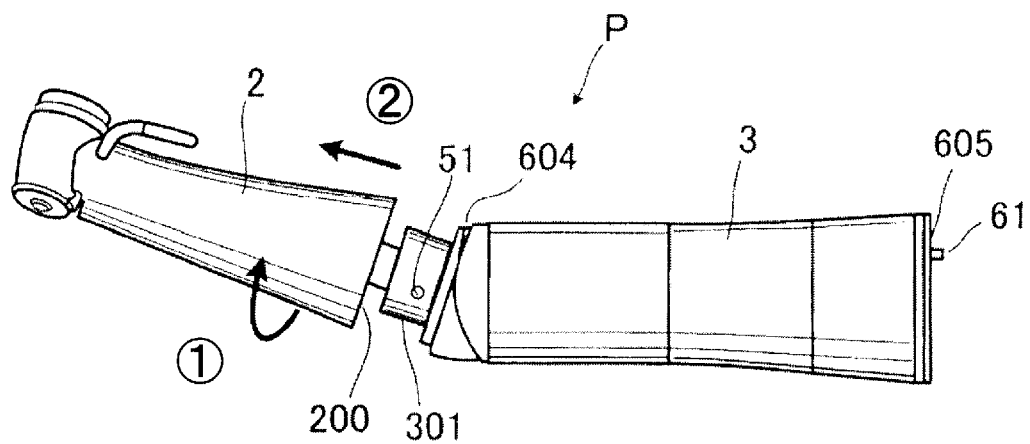
FIG. 8 is a side view illustrating the steps for disconnecting the neck section from the grip section.

Then, as shown in FIG. 8, the neck section 2 is rotated counterclockwise (as seen proximally from the neck section 2) relative to the grip section 3, with the guide of each engaging pin 51 released from the engaging portion 52 and travelling through the guide portion 54, until the engaging pin 51 reaches the entry portion 53. In this state, the neck section 2 and the grip section 3 are free to pull apart axially for disconnection. In this way, the neck section 2, the grip section 3, and the drive unit 4 are disassembled.

As discussed above, in the dental handpiece P according to the present invention, the neck section 2 and the grip section 3 are connected by means of the connecting means 5, which includes, on the side of the grip section 3, a pair of engaging pins projecting symmetrically and radially outwardly from the circumferential surface of the projection 301, and on the side of the neck section 2, a pair of engagement grooves formed on the inner surface of the neck housing 20 near the opening 200, each groove having the entry portion 53, the guide portion 54, and the engaging portion 52. With such connecting means 5, the neck section 2 and the grip section 3 may be connected simply by inserting the projection 301 of the grip section 3 into the neck housing 20 through the opening 200 with the engaging pins 51 aligned with the entry portions 53, further inserting the projection 301 until the engaging pins 51 enter the entry portions 53, and rotating the grip section 3 relative to the neck section 2, with the guide of the engaging pin 51 travelling from the entry portion 53 through the guide portion 54, until the engaging pin 51 fits in the engaging portion 52 to lock the connection between the neck section 2 and the grip section 3. Thus the neck section 2 and the grip section 3 may be connected easily and securely.

Further, the neck section 2 and the grip section 3 thus connected may be prevented from relative rotation by means of the detent pin 61, simply by connecting the drive unit 4 to the proximal end of the grip section 3 to distally press the detent pin 61, which then engages the catch means 63 (in this embodiment, the entry portion 53) in the neck section 2 to fix the engagement of the engaging pin 51 in the engaging portion 52.

In reverse, the neck section 2 and the grip section 3 may be released for relative rotation simply by detaching the drive unit 4 from the grip section 3, which causes the detent pin 61 to be withdrawn from the engagement in the catch means 63 under the force of the coil spring 62.

Then, simply by rotating the grip section 3 relative to the neck section 2 in the reverse direction until the engaging pin 51 aligns with the entry portion 53, the grip section 3 may be pulled apart from the neck section 2 easily.

In this embodiment, though the detent means 6 is associated with the connecting means 5, and the entry portion 53 of one of the engagement grooves is used as the catch means 63 for engagement with the distal end of the detent pin 61, a separate slit or hole may be provided in the proximal end of the neck section 2 for this purpose to achieve the same effect.

Though the connecting means 5 is employed for connection between the neck section 2 and the grip section 3, other conventional connecting means may alternatively be used. Preferably, the detent means 6 can interfere with the release of such connecting means as with the connecting means 5.

Figure 11:
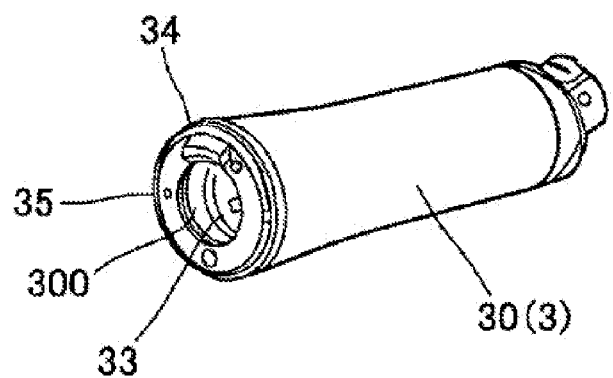
FIG. 11 is a perspective view of the grip section of an alternative embodiment of the handpiece, showing its external structure from the proximal side.
Figure 12:
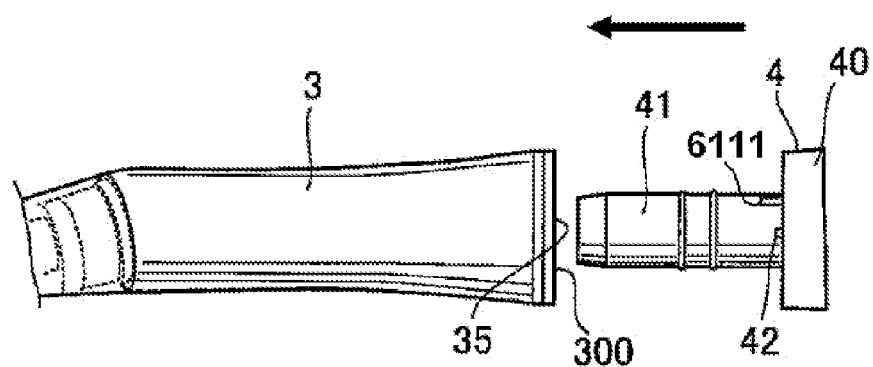
FIG. 12 shows the drive unit being connected to the grip section in an alternative embodiment of the handpiece.

Further, though the detent pin 61 is biased by the coil spring 62 to project out of the proximal end face of the grip section 3 in the rest position, a detent pin may alternatively be arranged in the grip section 3 such that the proximal end of the pin in the rest position is located inside the grip section 3 as shown in FIG. 11. In this case, a pressing member 6111 may be provided extending from the distal end face of the drive unit 4 for insertion into the grip section 3 and pressing the proximal end of the detent pin as shown in FIG. 12. When the drive unit 4 is connected to the grip section 3, the pressing member presses the detent pin on its proximal end to make it project out of the distal end face of the grip section 3 into engagement in the catch means 63 in the neck section 2 for preventing relative rotation of the neck section 2 and the grip section 3.

In this case, the catch means 63 in the neck section to be engaged with the detent pin may be the entry portion 53 of one of the engagement grooves, or may be provided separately from the entry portion.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising a head section to which a dental treatment tool is to be attached, a neck section of a generally cylindrical shape extending proximally from the head section, a grip section of a generally cylindrical shape detachably connected at its distal end to a proximal end of the neck section, and a drive unit which is detachably connected to a proximal end of the grip section, said handpiece comprising a detent unit for preventing relative rotation between the neck section and the grip section, said detent unit including:

a detent pin arranged in the grip section slidably in the axial direction of the grip section, a spring for biasing the detent pin proximally so that a distal end of the detent pin is arranged inside the grip section in a rest position, and a catch formed at a proximal end of the neck section for receiving a distal end of the detent pin for engagement, wherein said detent unit is arranged such that connection of the drive unit to the proximal end of the grip section causes the drive unit to press the detent pin distally against the proximal bias of said spring to compress the spring and to project said detent pin at its distal end out of a distal end face of the grip section into engagement with the catch, said engagement of the distal end of the detent pin with the catch preventing relative rotation between the neck section and the grip section, whereas disconnection of the drive unit from the proximal end of the grip section causes the detent pin to be released from pressure imposed by the drive unit, allowed to slide proximally under the proximal bias of said spring, and released from engagement with the catch.

2. The dental handpiece according to claim 1, wherein said detent pin is arranged in the grip section such that a proximal end of the detent pin in the rest position is projected from a proximal end face of the grip section, and wherein when the drive unit is connected to the proximal end of the grip section, the detent pin is pressed distally by a distal end face of the drive unit to project at its distal end out of the distal end face of the grip section.

3. The dental handpiece according to claim 1, wherein said detent pin is arranged in the grip section such that a proximal end of the detent pin in the rest position is located inside the grip section, wherein said drive unit has a pressing member extending from its distal end face and insertable into the grip section for pressing the detent pin, wherein when the drive unit is brought into connection to the proximal end of the grip section, the detent pin is pressed distally by the pressing member of the drive unit to project at its distal end out of the distal end face of the grip section.

4. The dental handpiece according to claim 1, wherein said grip section has at its distal end a generally cylindrical projection, and a pair of engagement pins projecting symmetrically on a circumferential surface of said projection, and wherein said neck section has an opening at its proximal end fittably receiving said cylindrical projection therein, and a pair of engagement grooves provided symmetrically on an inner surface near said opening for receiving said engaging pins, wherein each engagement groove has an engaging portion, an entry portion, and a guide portion, said engaging portion being capable of receiving and engaging one of the engagement pins in a lock position, said entry portion being opened to said opening of the neck section and extending in an axial direction of the neck section, said guide portion extending from an end of the entry portion opposite to said opening in a circumferential direction of the neck section for guiding the engaging pin from the entry portion to the engaging portion, and wherein the neck section and the grip section are connected by inserting the projection of the grip section into the neck section through the opening, with each engaging pin aligned with the entry portion of each engagement groove, and relatively rotating the neck section and the grip section with the guide of the engaging pins engaged in the guide portions until the engaging pins fit in the engaging portions in the lock position.

5. The dental handpiece according to claim 4, wherein the entry portion of at least one of the engagement grooves is used as said catch for receiving the distal end of the detent pin, and wherein said detent pin engages the entry portion, with said neck section and the grip section connected by engagement of the engaging pins in the engaging portions.

6. The dental handpiece according to claim 2, wherein when the drive unit is connected to the proximal end of the grip section, the proximal end of the detent pin is completely pressed inside the grip section.

7. The dental handpiece according to claim 1, wherein the detent pin has such a length that at least one end of the detent pin extends out of either end of the grip section, and the proximal end of the detent pin extends out of a hole in a proximal end face of the grip section under biasing force of the spring when the drive unit is not connected.

* * * * *